(12) United States Patent
Prima et al.

(10) Patent No.: US 9,650,707 B2
(45) Date of Patent: May 16, 2017

(54) METALLIC MATERIAL WITH AN ELASTICITY GRADIENT

(75) Inventors: Frédéric Prima, Paris (FR); Sophie Nowak, Paris (FR)

(73) Assignee: Centre National de la Recherch Scientifique, Paris (FR)

( * ) Notice: Subject to any disclaimer, the term of this patent is extended or adjusted under 35 U.S.C. 154(b) by 92 days.

(21) Appl. No.: 13/883,156

(22) PCT Filed: Nov. 4, 2011

(86) PCT No.: PCT/IB2011/054939
§ 371 (c)(1),
(2), (4) Date: May 29, 2013

(87) PCT Pub. No.: WO2012/059895
PCT Pub. Date: May 10, 2012

(65) Prior Publication Data
US 2013/0233456 A1 Sep. 12, 2013

(30) Foreign Application Priority Data
Nov. 4, 2010 (FR) ...................... 10 04327

(51) Int. Cl.
*C22C 14/00* (2006.01)
*C22F 1/18* (2006.01)
*A61C 8/00* (2006.01)
*C22F 1/00* (2006.01)
*A61L 27/06* (2006.01)

(52) U.S. Cl.
CPC ............ *C22F 1/183* (2013.01); *A61C 8/0012* (2013.01); *A61L 27/06* (2013.01); *C22C 14/00* (2013.01); *C22F 1/00* (2013.01); *A61L 2430/12* (2013.01); *C21D 2201/01* (2013.01); *C21D 2201/02* (2013.01); *C21D 2211/008* (2013.01)

(58) Field of Classification Search
CPC .................................. C22C 14/00; C22F 1/183
See application file for complete search history.

(56) References Cited

U.S. PATENT DOCUMENTS 4,542,539 A * 9/1985 Rowe, Jr. et al. ......... 623/23.57
5,447,580 A * 9/1995 Semiatin et al. ............. 148/565
2007/0137742 A1 6/2007 Hao et al.

OTHER PUBLICATIONS

Sun, F., et al., Influence of a short thermal treatment on the superelastic properties of a titanium-based alloy, Scripta Materialia 63 (2010) 1053-1056.*
International Search Report and Written Opinion for Application No. PCT/IB2011/054939 dated Feb. 28, 2012.
Sun, F. et al., Influence of a Short Thermal Treatment on the Superelastic Properties of a Titanium-Based Alloy, Scripta Materialia 63 (2010) 1053-1056.

* cited by examiner

*Primary Examiner* — Roy King
*Assistant Examiner* — Jophy S Koshy
(74) *Attorney, Agent, or Firm* — Alston & Bird LLP

(57) ABSTRACT

A monolithic titanium alloy having, in a temperature range ($\Delta T$) and at atmospheric pressure: an outer peripheral zone of a microstructure having a modulus of elasticity ($E_1$) and possessing superelastic properties in the range ($\Delta T$), and a core of a microstructure having a modulus of elasticity ($E_2$), and possessing elastic properties in the range ($\Delta T$); the microstructures and being different from one another, and the modulus of elasticity ($E_1$) being lower than said modulus of elasticity ($E_2$).

8 Claims, 2 Drawing Sheets

METALLIC MATERIAL WITH AN ELASTICITY GRADIENT

FIELD

The present invention relates to a metallic material having an elasticity gradient, the process for preparing the same and the use thereof, in particular for the production of dental implants.

BACKGROUND

The dental implants commonly used are generally made up of an externally threaded implant body, intended to be installed by screwing into the mandibular or maxillary bone, and of a part added onto the body, referred to as an inlay core or pillar, intended to be fastened to the body of the implant, after implantation, and equipped to receive a dental prosthesis (cf. FIGS. 1 and 2).

Dental implants generally consist of a titanium alloy (by way of example: Ti-6Al-4V), the modulus of elasticity (Young's modulus) of which lies in the vicinity of 90-110 GPa. However, the difference with the modulus of elasticity of human bone (30 GPa) is large, so that the stresses resulting from mastication are not transferred satisfactorily to the bone surrounding the implant, which may in the end give rise to a desorption of the bone and the loss of the implant in certain unfavorable clinical cases.

Therefore, this poor stress transfer may lead either to insufficient mechanical stimulation, or on the contrary to peaks of stresses and strains in the peri-implant bone. In either case, this may de detrimental to the osteointegration of the implant and constitutes a limitation to the use of the implants in certain parts of the buccal sphere, especially in the sites where there is only a small amount of bone or the bone is of insufficient quality.

SUMMARY

A material has now been developed that possesses an elasticity gradient. More specifically, this material is characterized by superelastic properties at the surface and elastic properties at the core, the apparent modulus of elasticity at the surface furthermore being much lower than that at the core of the material.

This material is particularly useful for producing a novel type of dental implant. Thus, it is possible to obtain a material according to the invention that possesses, on the outer face of the implant (implant/bone interface) an apparent modulus of around 30 GPa very close to that of the bone, and on the inner face of the same implant (implant/pillar interface) a modulus of around 80 GPa that makes it possible to ensure the stiffness of the implant/pillar/prosthesis assembly. By providing a better transfer of the stresses from the implant to the bone, this material makes it possible to dissipate a portion of the mechanical energy deriving from functional stresses (mastication) and to avoid the peaks of stresses and strain in the peri-implant bone. This advantageously leads to a stimulation of the bone remodeling, and therefore a better osteointegration of the implant.

Due to these properties, this material advantageously offers the possibility of designing dental implants for sites of the buccal sphere where direct implantation is not generally possible and requires resulting to surgery, for example in the case of implant sites where there is only a small amount of bone or the bone is of insufficient quality.

Moreover, this material may be prepared according to economic and reliable processes that are easy to implement and can easily be transposed to the industrial scale.

Metallic Material (M) having an Elasticity Gradient

Thus, a first subject of the invention relates to a monolithic metallic material (M) comprising, in a temperature range ($\Delta T$) and at atmospheric pressure:
- at least one outer peripheral zone consisting of a microstructure ($m_1$) having a modulus of elasticity ($E_1$) and possessing superelastic properties in said range ($\Delta T$), and
- a core consisting of a microstructure ($m_2$) having a modulus of elasticity ($E_2$), and possessing elastic properties in said range ($\Delta T$);
- said microstructures ($m_1$) and ($m_2$) being different from one another, and
- said modulus of elasticity ($E_1$) being lower than said modulus of elasticity ($E_2$).

As used here, "monolithic" metallic material means a material consisting of one and the same metallic element or one and the same combination of metallic elements, for example an alloy of titanium and niobium (Ti—Nb), unlike, in particular, materials referred to as "composites" which are characterized by the presence of at least one interface between two different materials. This does not exclude the chemical composition of a monolithic alloy from varying in the various crystalline phases or even in the various zones of the sample. The material M is in particular a part made of material M, such as an ingot or a bar.

The expressions "microstructure" or "microstructural state" are used here interchangeably, and refer to the inner structure of the metallic material, at a scale generally between 10 mm and 100 µm. The microstructure of a material plays an important role since it influences a large number of properties, in particular the mechanical properties of the material. As a general rule, the microstructure of a material is mainly characterized by the characteristics of the solid solution of the material, the arrangement of the phases, the size of the grains and the porosity. The solid solution is characterized in particular by the ordered or disordered, crystalline or amorphous nature of the solid solution and also the defects, such as the concentration of vacancies, and the solutes optionally present. The techniques for characterizing the micro-structure of a material are very varied. A distinction is made in particular between morphological characterization techniques and the techniques for characterizing the structure of the materials. Among the morphological characterization techniques, mention may especially be made of optical microscopy (OM), scanning electron microscopy (SEM), or transmission electron microscopy (TEM). For further information regarding these techniques, reference could in particular be made to the file M260 from Techniques de l'Ingénieur (Engineer Techniques). Identification of the phases is generally carried out by X-ray diffraction.

The "modulus of elasticity" also referred to as the "Young's modulus" is the constant which connects the tensile (or compressive) stress applied to a material ($\sigma$) and the strain (relative elongation) which results therefrom ($\epsilon$) for an isotropic elastic material, as long as the strain remains small and the elasticity limit of the material is not reached: $\sigma = E\epsilon$ (Hooke's law). The modulus of elasticity characterizes the stiffness of the material.

As a general rule, for metallic materials, the modulus of elasticity is a quantity linked to the stiffness of the atomic bonds and it is consequently constant for a given atomic composition. This is what is denoted here, in the present description, by "elastic properties" or else conventional elasticity, also referred to as enthalpic or intrinsic elasticity: the mechanical stress applied to the material does not lead to phase transformation within the material.

"Superelastic" materials are materials for which the application of a stress induces a phase transformation, via a reversible martensitic transformation. Thus, by way of example, the superelastic titanium alloys of centered cubic structure (also denoted by β structure) are transformed under stress, reversibly, into the orthorhombic phase (also denoted by α" structure) of the same composition at a temperature equal to or slightly above the martensitic transformation temperature Ms.

"Apparent modulus of elasticity" characterizes the apparent stiffness (that is to say the relationship between stress and strain) of the superelastic material in the temperature and stress range in which it undergoes the martensitic phase transformation.

The "martensitic transformation" denotes a transformation via which the high-temperature phase, referred to as austenitic phase, changes from a crystalline structure in order to adopt a less symmetrical structure referred to as martensitic structure. In the case of shape memory materials, and in particular superelastic materials, this transformation is reversible so that, after raising the temperature or reversing of the stress, the inverse transformation occurs. The cooling start temperature or martensitic transformation temperature is generally denoted by temperature Ms, and the finish temperature is denoted by Mf. The start and finish temperatures of the inverse or austenitic transformation are generally denoted As and Af respectively. When the temperature is above Af, the martensite induced under stress is not stable and returns to the austenite phase as soon as the stress is relaxed. The temperatures Ms, Mf, As and Af generally vary with the chemical composition of the metallic material.

Within the meaning of the present description, the expression "outer peripheral zone", or else the term "surface" are used here interchangeably and refer to a zone of the material (M) in contact with the outside and the thickness of which may vary from a few microns to a few hundreds of micrometers, in particular from 100 μm to 1 mm.

Preferably, the material (M) comprises a one and only outer peripheral zone as defined above.

According to one preferred variant of the invention, the range (ΔT) is a range corresponding to the usage conditions of the metallic material.

Preferably, (ΔT) includes or is slightly above the martensitic transformation temperature (Ms) of the microstructure ($m_1$) at atmospheric pressure. Preferably, (ΔT) is between (Ms−50)° C. and (Ms+100)° C. Thus, during the use of the material (M) as a dental implant for example, at a usage temperature within the range (ΔT), the surface of the material will undergo, at the usage temperature, a martensitic transformation which will make it possible to reduce the apparent modulus. Preferably, (ΔT) is a temperature between 35° C. and 40° C. at atmospheric pressure.

According to one preferred aspect, the metallic material (M) is biocompatible.

The term "biocompatible" is understood to mean a material which is suitable for coming into contact with human or animal tissues, without inducing excessive toxicity, inflammation, in particular irritation, or an allergic response, or another undesirable side effect, and which offers an acceptable benefit/risk ratio.

Preferably, the metallic material (M) is an alloy of titanium, preferably of type β, in particular an alloy in which the titanium represents around 75% or at least 70% (at. %) of the metallic material (M), in particular an alloy that also comprises niobium. The percentages indicated here, expressed in atomic % (at. %), refer to the molar fraction of titanium in the material, i.e. to the number of moles of titanium per hundred moles of atoms of the material.

By way of example, mention may especially be made of the alloy Ti-24Nb or Ti-20Nb-6Zr. Indeed, titanium alloys are particularly advantageous due to their biocorrosion resistance, their biocompatibility and their mechanical properties, in particular their low modulus of elasticity, which may be relatively close to that of bone.

Preferably, the microstructure ($m_1$) consists of a (centered cubic) β phase.

Preferably, the microstructure ($m_2$) comprises a β phase and an (orthorhombic) α" phase.

According to one preferred aspect, the difference between the moduli of elasticity $E_2$ and $E_1$ is greater than 20 GPa.

According to a preferred variant, the apparent modulus of elasticity $E_1$ is between 20 and 50 GPa, i.e. a value very close to the modulus of elasticity of bone.

According to one preferred variant, $E_2$ is between 70 and 90 GPa.

Advantageously, the modulus of elasticity ($E_1$) is between 10 and 30 GPa and the modulus of elasticity ($E_2$) is between 70 and 90 GPa. This embodiment is particularly advantageous for the production of dental implants. The outer surface of the material (M) in contact with the bone has a modulus ($E_1$) very close to that of bone, which makes it possible to ensure an optimized transfer of the functional stresses and to dissipate a portion of the mechanical energy. The core of the material (M), intended to form the inner face of the same implant, in contact with the pillar, has a high modulus of elasticity ($E_2$) making it possible to ensure the stiffness of the implant/pillar/prosthesis assembly.

Dental Implant

A second subject of the invention relates to a metallic material (M) as defined above for the use thereof as an implant in an individual, in particular for the use thereof as dental implant.

According to another subject, the invention relates to a dental implant comprising or consisting of a metallic material as defined in the present description.

The invention relates in particular to a dental implant comprising an implant body consisting of a metallic material as defined above.

Processes for Preparing the Metallic Material M Having an Elasticity Gradient

According to another subject, the invention also relates to two processes for preparing materials (M) as defined above. These processes are each based on a simple thermomechanical treatment that makes it possible to create a microstructure gradient ($m_1$, $m_2$), that is the cause of an elasticity gradient ($E_1$, $E_2$), within a monolithic metallic material M which may have, for certain microstructures, superelastic properties in a range (ΔT) as defined above and at atmospheric pressure. These two processes use, in particular, the "transient state" linked to any heat transfer, and in particular the gradient of change of the microstructure from an initial controlled state: severely deformed state in the case of the process A referred to as "flash annealing", or single-phase beta state, in the case of the process B referred to as "quenching".

The invention also relates to a third process (C) referred to as "preferential dissolution".

Process A—"Flash Annealing"

According to one aspect, the invention relates to a process for preparing a metallic material (M) having an elasticity gradient as defined above, comprising the steps of:
i) cold working of a monolithic metallic material (M), so as to generate a microstructural state ($m_0$);
ii) heat treatment of said material obtained in step (i) at a temperature between 500° C. and 800° C., for a short enough time so as to obtain a material (M) comprising microstructural states ($m_1$) and ($m_2$) different from ($m_0$), and moduli of elasticity ($E_1$, $E_2$), as defined above.

This process leads to a microstructure gradient being obtained, created by the difference in the degree of recrystallization between the surface and the core of the material M. At the surface, the treatment leads to a significant recrystallization giving a grain micro-structure ($m_1$) which locally induces a reversible superelasticity and a lowering of the apparent elastic modulus to a value ($E_1$). At the core of the material M, the recrystallization process remains incomplete and therefore enables the material to remain work-hardened, thus preventing superelastic properties from being obtained: the elastic modulus ($E_2$) is therefore locally higher than at the surface (modulus of elasticity $E_1$). This process is therefore based on the use of a temperature gradient, here during step ii), also referred to as "flash annealing", in order to create a microstructure gradient ($m_1 \neq m_2$) and therefore elasticity gradient ($E_1 \neq E_2$).

The expression "cold working" is understood to mean a deformation carried out at a temperature that does not enable the material to be restored. It therefore retains all the signs of the plastic deformation at the end of the operation (dislocations, twinned crystals, stress-induced martensitic phase, etc). At the end of this step, the material M is in one and the same microstructural state $m_0$, uniform throughout the sample. The material M may especially be shaped in the form of a bar by drawing.

The temperature chosen to carry out the heat treatment in step ii) is a temperature that makes it possible to obtain the recrystallization of the outer periphery of the material M under a microstructure ($m_1$) having a modulus of elasticity ($E_1$) and superelastic properties at atmospheric pressure and in a range ($\Delta T$). This recrystallization temperature makes it possible to recrystallize the phase which, under stress, is transformed, forming small grains and without other precipitates. It depends in particular on the chemical composition of the monolithic material M, whereas the kinetics of this recrystallization step is also a function of the thermomechanical stresses undergone by the material. The recrystallization temperature of a given metallic material may be easily determined by a person skilled in the art by routine tests, for example by electrical resistivity measurements or by differential calorimetry.

Preferably, the metallic material (M) is a titanium alloy.

According to a preferred aspect, the cold working of the material ($m_0$ is carried out in step i) at a temperature between 15° C. and 200° C., in particular when M is a superelastic titanium alloy.

Preferably, the heat treatment in step ii) is carried out at a temperature between 500° C. and 800° C., in particular between 500° C. and 700° C., especially at 600° C., in particular when M is a superelastic titanium alloy.

According to this process, the heat treatment is carried out over a short enough time to obtain a material M having an elasticity gradient as defined previously, i.e. a material (M) comprising at least two microstructural states $m_1$ and $m_2$, respectively having the moduli of elasticity $E_1$ and $E_2$ as defined above. By way of example, a time between 30 seconds and 6 minutes is generally sufficient, especially when the process is applied to a material (M) having a maximum thickness of 0.5 mm, i.e. a thickness of less than 0.5 mm. The time that is needed and that is sufficient for obtaining the microstructure gradient and elasticity gradient can easily be determined by a person skilled in the art according to conventional techniques.

According to one variant, the process according to the invention also comprises a subsequent step of machining the material (M) obtained.

By way of example, the material (M) obtained in step ii) may be a cylinder or ingot which is then machined so as to give it a form suitable for the use for which the material is intended, for example in the form of a dental implant.

According to another preferred embodiment, the process also comprises a step of machining the material ($m_0$) so as to make it acquire a shape suitable for the desired use before the heat treatment step ii), in particular a form suitable for use as a dental implant.

Process B—"Quenching"

According to another aspect, the invention relates to a process for preparing a metallic material (M) having an elasticity gradient as defined above, comprising the steps of:
i) solution treatment of a monolithic metallic material (M), at a temperature within the stability range of the β phase, preferably for sufficient time to obtain a material that is homogeneous from the point of view of the chemical composition and of the crystalline phase; and
ii) quenching of the material obtained in step i) so as to obtain a metallic material (M) having an elasticity gradient as defined above.

The expression "solution treatment" is understood to mean a heat treatment in which the material is maintained at a sufficient temperature, and for a long enough time, so that the non-stable precipitates disappear, the atoms diffuse and the material is finally homogeneous (crystalline phases present and chemical composition). Typically, this temperature lies, for the titanium alloys, at a temperature of 50° C. above the beta transus.

For titanium alloys, the phase that can be transformed under stress, i.e. the centered cubic (or β) phase is stable at high temperature (around 850° C.). The solution treatment step i) of the titanium alloys may thus be carried out at a temperature between 800° C. and 1000° C., preferably under a high vacuum between $10^{-5}$ and $10^{-7}$ Pa, or else under a controlled atmosphere in the presence of an inert gas such as argon or helium. The quenching step ii) makes it possible to keep it the same, at ambient temperature if the composition is well chosen and the cooling rate sufficient. The phase obtained is stable through to at least 100° C.

In order to obtain a microstructure gradient ($m_1$, $m_2$) and elasticity gradient ($E_1$, $E_2$) as defined in the present application, this process uses the natural quenchability of metallic materials. Indeed, for a monolithic metallic material, the cooling rate is in particular a function of the thermal diffusivity of the material and is generally much greater at the edges than at the center. It is thus possible to control the cooling rate gradient by adapting the severity of the quenching medium (from the most severe medium: water, to the least severe medium: air). In this way, it is possible to create a microstructure gradient ($m_1$, $m_2$) that makes it possible to obtain an elastic gradient ($E_1$, $E_2$). The severely quenched material at the surface has a single-phase microstructure ($m_1$) capable of undergoing a martensitic transformation under stress, and having a low elastic modulus ($E_1$). A contrario, according to this process, the core of the material remains imperfectly quenched, which induces the precipitation of additional phases which prevent the same martensitic transformation. This phenomenon is the cause of the desired elastic modulus gradient.

Preferably, step i) is carried out at a temperature between 800° C. and 900° C.

Preferably, the quenching step is carried out in a medium having a low enough severity to enable a material (M) having an elasticity gradient as defined above to be obtained. The "severity" of the quenching medium is defined here as the ability of the medium to discharge the thermal energy of the material M.

Preferably, the severity of the quenching medium is less than or equal to that of water. According to one embodiment, the quenching is carried out in water.

Indeed, if the severity of the medium is insufficient, the cooling rate of the material will be such that other phases may be formed at the core. However, these phases may locally reduce the proportion of the centered cubic phase within the material and thus decrease the superelastic nature of the material M. When they are present in a significant proportion, they may even lead to the complete stability of the material. Without superelasticity, the modulus is then higher (70-80 GPa, versus 30-40 GPa with the superelastic effect for titanium alloys).

Process C—"Preferential Dissolution"

According to another aspect, the invention relates to a process for preparing a monolithic titanium alloy (M) as defined above, comprising the steps of:

i) first heat treatment of a titanium alloy (M), at a temperature where said alloy has an ($\alpha+\beta$) two-phase microstructure ($m_2$), for a long enough time so that the microstructure ($m_2$) is homogeneous throughout the volume of the alloy;

ii) second heat treatment of the alloy of micro-structure ($m_2$) obtained at a temperature above the $\beta$ transus of said alloy, for a short enough time to obtain:
  a transformation of the ($\alpha+\beta$) two-phase microstructure ($m_2$) into a $\beta$ single-phase micro-structure ($m_1$) over the outer peripheral zone of the alloy, and
  a conversion of the ($\alpha+\beta$) two-phase micro-structure ($m_2$) at the core of the alloy, whereby a titanium alloy (M) is obtained that comprises the microstructural states ($m_1$) and ($m_2$), and the moduli of elasticity ($E_1$, $E_2$), as defined above.

Step i) is carried out in the temperature range where the alloy has an "($\alpha+\beta$)" two-phase microstructure, that is to say in the precipitation range of the $\alpha$ phase.

The time during which this treatment is carried out varies with the volume of the material. The greater this volume, the longer the duration of this heat treatment.

Step ii) is carried out at a temperature above the $\beta$ transus of the alloy. The $\beta$ transus, which is a constant temperature for an alloy of given chemical composition, may be easily measured by methods well known to a person skilled in the art.

This step is carried out for a short enough time so that the dissolution of the $\alpha$ phase to $\beta$ phase only has time to occur over the outer peripheral zone of the material (M), the ($\alpha+\beta$) two-phase microstructure, at the core of the material (M) remaining unchanged.

The alloy thus obtained comprises an outer peripheral zone consisting of a $\beta$ single-phase microstructure $m_1$ and a core consisting of an ($\alpha+\beta$) two-phase microstructure $m_2$.

Since the ($\alpha+\beta$) two-phase microstructure has a modulus of elasticity $E_2$ much greater than the modulus of elasticity $E_1$ of the $\beta$ single-phase microstructure, the microstructure gradient ($m_1$, $m_2$) produces an elasticity gradient ($E_1$, $E_2$) from the periphery toward the center of the alloy.

According to another subject, the invention relates to a metallic material (M) capable of being obtained according to one of the processes defined above.

The examples which follow are given by way of illustration and non-limitingly.

BRIEF DESCRIPTION OF THE DRAWINGS

Figures

DETAILED DESCRIPTION

Examples

The alloy of composition Ti-24Nb (at. %) is obtained by arc melting of the two pure metals. The composition of this 20 g ingot is homogenized by a heat treatment at 950° C. for 20 hours, under a high vacuum of $10^{-6}$ Pa. The sample is then quenched after an annealing at 850° C. for 360 s, for the purpose of retaining the high-temperature beta phase, which is more ductile than the stable phase at low temperature: the alpha phase. Drawing at ambient temperature then makes it possible to pass from an ingot having a diameter of around 11 mm to a rod having a diameter of 4 mm. A 2 mm slice is cut in order to characterize the material in the "cold drawn" state. Another piece which is 1 cm long is also cut from the drawn rod, then annealed for 360 s at 600° C. in a silica tube filled with helium and submerged in salt baths. At the end of this time, the tube is cooled rapidly in water.

Two cross sections of the cylinder are cut, after annealing, with a thickness of 2 mm. One originates from the end of the cylinder ("flash annealed T1") and will make it possible to analyze the microstructure and the mechanical behavior at the surface, the other is extracted from the middle ("flash annealed T2") and will make it possible to visualize whether the temperature gradient during the annealing creates a visible gradient for the microstructure and the mechanical behavior.

The X-ray diffraction equipment is a Philips PW1710 machine with a copper tube ($\lambda_{K\alpha 1}$=1.542 Å) operating at 40 kV and 25 mA. The instrumented microindenter is a CSM indenter. The tip used is made of diamond and is of Vickers type. The force F and the displacement h of the tip are recorded during a cycle in which the maximum force is 3000 mN (achieved in 30 s). The unloading portion is purely elastic, it is therefore directly linked to the Young's modulus. The calculation follows the conventional models of Sneddon, who links the slope at the start of unloading and the Young's modulus, and of Oliver and Pharr, who link the measured depth h to the actual depth $h_c$ [ref].

The projected contact area, necessary for the estimation of E, was calibrated by being based on the measurement of fused silica. The result is the following:

$$A_c = 24.5 \times h_c^2 + 1190 \times h_c$$

The area function for an ideal Vickers indenter is $24.5\, h_c^2$, the additional term takes into account the geometry defects. 20 tests were carried out every 100 μm along a radius.

Figure 1:
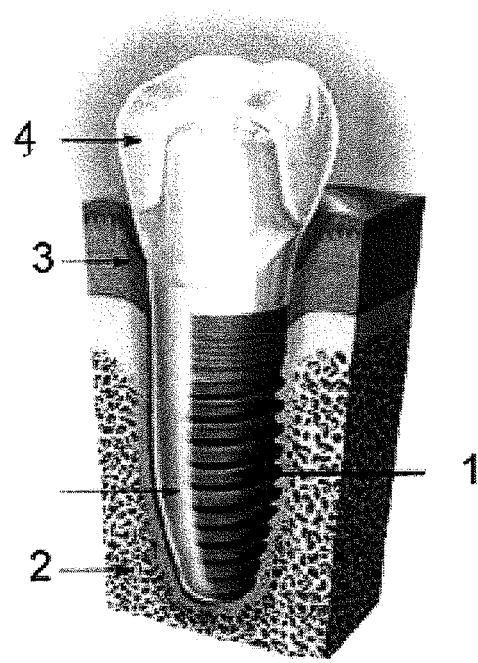
FIG. 1: representation of a dental implant (1) installed in the maxillary bone (2) and surmounted by a prosthesis (4) level with the gum (3).
Figure 2:
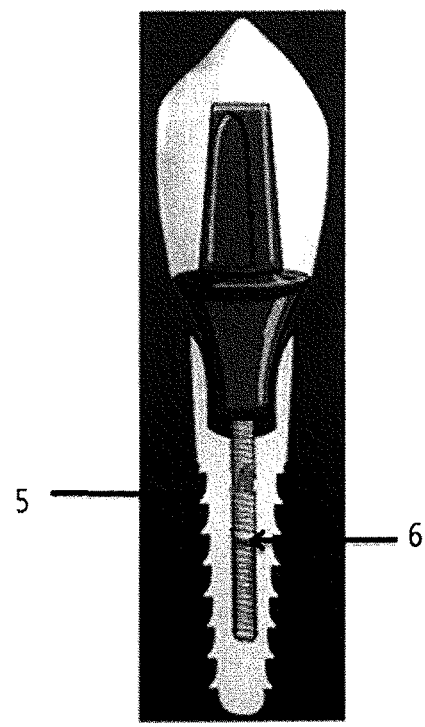
FIG. 2: representation of a dental implant comprising an implant body (5) intended to receive a pillar (6) that makes it possible to attach the prosthesis.
Figure 3:
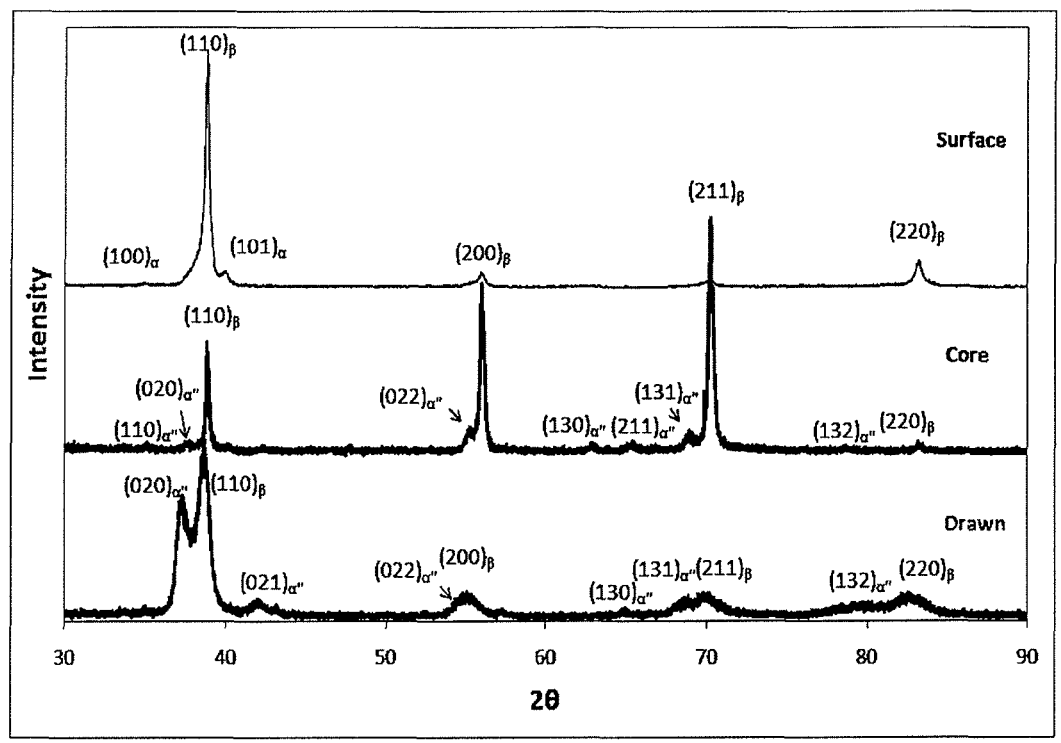
FIG. 3: diffraction spectra for three samples: drawn (cold drawn), surface (flash annealed T1) and core (flash annealed T2).

The microstructure of the "cold drawn", "flash annealed T1" and "flash annealed T2" samples is estimated by X-ray diffraction (FIG. 3). The idea is to compare the diffraction diagrams in order to estimate the effect of the temperature gradient on the microstructure. The cold drawn sample has broad peaks and a large proportion of α" phase. These two aspects are the result of the defects induced by the plastic deformation: a large dislocation density and martensitic phase induced under residual strain. The "flash annealed T2" sample is textured since the main β peak is (211) and not (110). It is also possible to identify the β and α" phases. The result is relatively close to the "cold drawn" sample, but two significant differences can be indicated: the peaks are narrower and the proportion of α" phase is smaller. The "flash annealed T1" sample is composed of the β phase mainly and of a few percent of α. This means that the α" phase disappears and the β phase recrystallizes. The energy is even sufficient to form a few α crystals.

These results represent an average microstructure of the various cross sections: "cold drawn", "flash annealed T1" and "flash annealed T2". The first two are, a priori, homogeneous but the third is seemingly heterogeneous. Indeed, the peripheral zone for T2 is identical to T1 since it is a question of surface.

However, the diffraction spectrum of T2 principally shows a textured β phase in the presence of α". The conclusion is, consequently, that the sample T2 has a microstructure gradient and that the proportion of α" is probably greater at the center of the sample than that which it is possible to estimate by X-ray diffraction.

Figure 4:
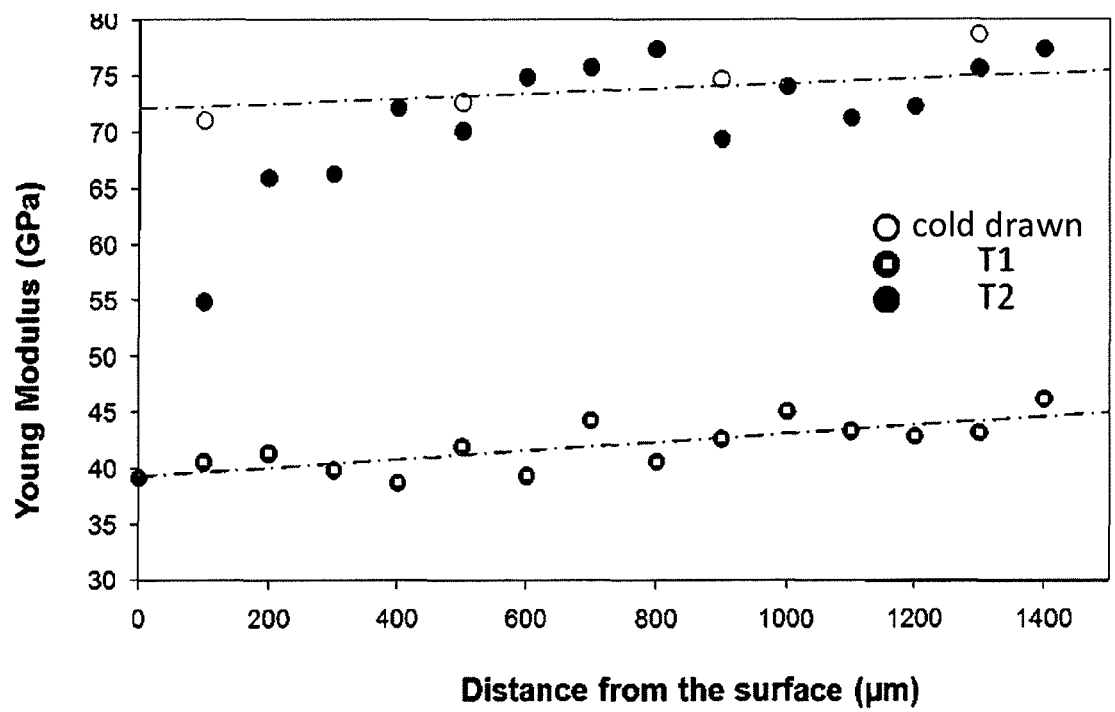
FIG. 4: Young's modulus measured by instrumented microindentation along a radius for three samples: cold drawn, flash annealed T1 and flash annealed T2.

The mechanical behavior was then studied locally by instrumented microindentation. FIG. 4 presents the Young's modulus values for the three samples. E is constant along the radius for the "cold drawn" sample (75 GPa) and the "flash annealed T1" sample (40 GPa). For the flash annealed T2 sample, the modulus increases gradually from 40 GPa to 75 GPa over a zone around 400 μm, and then remains constant. This demonstrates that the microstructure gradient may have an effect on the elastic behavior, for this composition and under these production conditions.

The invention claimed is:

1. A monolithic titanium alloy comprising, in a temperature range (ΔT) and at atmospheric pressure:
    at least 70 atomic % of titanium based on the total atomic % of titanium alloy, the alloy also comprising niobium;
    a one and only outer peripheral zone consisting of a microstructure ($m_1$) having a modulus of elasticity ($E_1$) and possessing superelastic properties in said temperature range of 35 to 40° C., and
    a core consisting of a microstructure ($m_2$) having a modulus of elasticity ($E_2$), and possessing elastic properties in said range of temperature of 35 to 40° C.;
    said microstructures ($m_1$) and ($m_2$) being different from one another, and
    the difference between said modulus of elasticity ($E_1$) and said modulus of elasticity ($E_2$) being greater or equal to 20 GPa.

2. The titanium alloy as claimed in claim 1, wherein $E_1$ is between 20 and 50 GPa.

3. The titanium alloy as claimed in claim 1, wherein $E_2$ is between 70 and 90 GPa.

4. An implant comprising the titanium alloy as claimed in claim 1.

5. A dental implant comprising the titanium alloy as claimed in claim 1.

6. A dental implant consisting of the titanium alloy as defined in claim 1.

7. The dental implant as claimed in claim 5, comprising an implant body consisting of a metallic material.

8. The titanium alloy as claimed in claim 1, wherein the alloy is in the form of a bar, a cylinder, an ingot, an implant body or a dental implant.

* * * * *